United States Patent
Ash et al.

(10) Patent No.: US 11,955,829 B2
(45) Date of Patent: Apr. 9, 2024

(54) POWER SOURCE CHARGING FOR NEGATIVE PRESSURE WOUND THERAPY APPARATUS

(71) Applicant: Smith & Nephew Asia Pacific Pte. Limited, Singapore (SG)

(72) Inventors: Matthew Ash, Cambridge (GB); Damyn Musgrave, Cottenham (GB); Felix Clarence Quintanar, Hull (GB)

(73) Assignee: Smith & Nephew Asia Pacific Pte. Limited, Singapore (SG)

( * ) Notice: Subject to any disclaimer, the term of this patent is extended or adjusted under 35 U.S.C. 154(b) by 798 days.

(21) Appl. No.: 17/043,415

(22) PCT Filed: Apr. 29, 2019

(86) PCT No.: PCT/IB2019/053507
§ 371 (c)(1),
(2) Date: Sep. 29, 2020

(87) PCT Pub. No.: WO2019/211730
PCT Pub. Date: Nov. 7, 2019

(65) Prior Publication Data
US 2021/0106735 A1    Apr. 15, 2021

(30) Foreign Application Priority Data

Apr. 30, 2018   (GB) ..................... 1806988

(51) Int. Cl.
*H02J 7/00* (2006.01)
*A61M 1/00* (2006.01)

(52) U.S. Cl.
CPC ...... *H02J 7/007194* (2020.01); *H02J 7/0048* (2020.01); *A61M 1/962* (2021.05);
(Continued)

(58) Field of Classification Search
None
See application file for complete search history.

(56) References Cited

U.S. PATENT DOCUMENTS

| D239,019 S | 3/1976 | Flinn |
| 4,498,850 A | 2/1985 | Perlov et al. |

(Continued)

FOREIGN PATENT DOCUMENTS

| DE | 102015215165 A1 | 2/2017 |
| EP | 0883430 B1 | 1/2007 |

(Continued)

OTHER PUBLICATIONS

International Search Report and Written Opinion for Application No. PCT/IB2019/053507, dated Aug. 21, 2019, 10 pages.

(Continued)

*Primary Examiner* — David V Henze-Gongola
(74) *Attorney, Agent, or Firm* — Knobbe, Martens, Olson & Bear, LLP

(57) ABSTRACT

Embodiments of negative pressure wound therapy devices, systems and methods are disclosed. In some embodiments, a negative pressure wound therapy device includes a negative pressure source configured to provide negative pressure to a wound via a fluid flow path, a power source configured to power the negative pressure source, and a charging circuit configured to monitor a temperature of the power source and charge the power source. The charging circuit can be further configured to in response to a determination that the temperature of the power source is below a temperature threshold, provide a first charging power to the power source. The charging circuit can be further configured to in response to a determination that the temperature of the power source has reached or is above the temperature threshold, lower the first charging power to a second charging power.

20 Claims, 7 Drawing Sheets

(52) U.S. Cl.
CPC ............... *A61M 2205/3331* (2013.01); *A61M 2205/583* (2013.01); *A61M 2205/8206* (2013.01); *A61M 2205/8237* (2013.01)

(56) References Cited

U.S. PATENT DOCUMENTS

| | | | |
|---|---|---|---|
| 4,731,076 | A | 3/1988 | Noon et al. |
| D357,735 | S | 4/1995 | Mcphee |
| 5,514,088 | A | 5/1996 | Zakko |
| 5,712,795 | A | 1/1998 | Layman et al. |
| 6,027,490 | A | 2/2000 | Radford et al. |
| 6,203,291 | B1 | 3/2001 | Stemme et al. |
| 6,232,680 | B1 | 5/2001 | Bae et al. |
| 6,396,407 | B1 | 5/2002 | Kobayashi |
| D475,132 | S | 5/2003 | Randolph |
| 7,004,915 | B2 | 2/2006 | Boynton et al. |
| 7,022,113 | B2 | 4/2006 | Lockwood et al. |
| 7,070,584 | B2 | 7/2006 | Johnson et al. |
| 7,214,202 | B1 | 5/2007 | Vogel et al. |
| D581,042 | S | 11/2008 | Randolph et al. |
| D590,934 | S | 4/2009 | Randolph et al. |
| D602,582 | S | 10/2009 | Pidgeon et al. |
| D602,583 | S | 10/2009 | Pidgeon et al. |
| D602,584 | S | 10/2009 | Pidgeon et al. |
| 7,608,066 | B2 | 10/2009 | Vogel |
| 7,611,500 | B1 | 11/2009 | Lina et al. |
| 7,857,806 | B2 | 12/2010 | Karpowicz et al. |
| 7,927,319 | B2 | 4/2011 | Lawhorn |
| D645,137 | S | 9/2011 | Gonzalez |
| 8,021,348 | B2 | 9/2011 | Risk, Jr. et al. |
| 8,062,272 | B2 | 11/2011 | Weston |
| 8,066,243 | B2 | 11/2011 | Svedman et al. |
| 8,070,735 | B2 | 12/2011 | Koch et al. |
| D654,164 | S | 2/2012 | Cole et al. |
| D660,409 | S | 5/2012 | Taggerty et al. |
| 8,215,929 | B2 | 7/2012 | Shen et al. |
| 8,216,197 | B2 | 7/2012 | Simmons et al. |
| 8,226,620 | B2 | 7/2012 | Giezendanner et al. |
| 8,308,714 | B2 | 11/2012 | Weston et al. |
| 8,317,774 | B2 | 11/2012 | Adahan |
| 8,366,692 | B2 | 2/2013 | Weston et al. |
| 8,409,160 | B2 | 4/2013 | Locke et al. |
| 8,480,641 | B2 | 7/2013 | Jacobs |
| 8,540,688 | B2 | 9/2013 | Eckstein et al. |
| 8,641,693 | B2 | 2/2014 | Locke et al. |
| 8,668,677 | B2 | 3/2014 | Eckstein et al. |
| 8,858,517 | B2 | 10/2014 | Pan et al. |
| 8,905,985 | B2 | 12/2014 | Allen et al. |
| 9,050,398 | B2 | 6/2015 | Armstrong et al. |
| 9,084,845 | B2 | 7/2015 | Adie et al. |
| 9,138,531 | B2 | 9/2015 | Yodfat et al. |
| 9,199,010 | B2 | 12/2015 | Yao et al. |
| D750,222 | S | 2/2016 | Chang |
| D750,235 | S | 2/2016 | Maurice |
| D750,236 | S | 2/2016 | Maurice |
| D757,260 | S | 5/2016 | Lombardi, III et al. |
| 9,327,063 | B2 | 5/2016 | Locke et al. |
| 9,333,281 | B2 | 5/2016 | Giezendanner et al. |
| D764,047 | S | 8/2016 | Bjelovuk et al. |
| D764,048 | S | 8/2016 | Bjelovuk et al. |
| D764,653 | S | 8/2016 | Bjelovuk et al. |
| D764,654 | S | 8/2016 | Bjelovuk et al. |
| 9,415,199 | B2 | 8/2016 | Tsai |
| 9,427,505 | B2 | 8/2016 | Askem et al. |
| D765,830 | S | 9/2016 | Bjelovuk et al. |
| 9,445,948 | B2 | 9/2016 | Smola |
| D773,658 | S | 12/2016 | Bow |
| 9,586,036 | B2 | 3/2017 | Masuda et al. |
| D788,293 | S | 5/2017 | Eckstein et al. |
| D791,939 | S | 7/2017 | Turturro et al. |
| D792,586 | S | 7/2017 | Becker |
| 9,737,649 | B2 | 8/2017 | Begin et al. |
| D797,275 | S | 9/2017 | Evans et al. |
| 9,901,664 | B2 | 2/2018 | Askem |
| 9,923,401 | B2 | 3/2018 | Jung |
| 10,124,093 | B1 | 11/2018 | Francis et al. |
| 10,143,785 | B2 | 12/2018 | Adams et al. |
| 10,155,070 | B2 | 12/2018 | Childress et al. |
| D842,460 | S | 3/2019 | Gierse et al. |
| D851,759 | S | 6/2019 | Jones et al. |
| D852,356 | S | 6/2019 | Steele et al. |
| 2002/0013545 | A1 | 1/2002 | Soltanpour et al. |
| 2002/0030002 | A1 | 3/2002 | Verkaart et al. |
| 2002/0098097 | A1 | 7/2002 | Singh |
| 2002/0161317 | A1 | 10/2002 | Risk et al. |
| 2004/0068224 | A1 | 4/2004 | Couvillon, Jr. et al. |
| 2005/0234485 | A1 | 10/2005 | Seegert et al. |
| 2006/0281398 | A1 | 12/2006 | Yokomizo et al. |
| 2008/0234641 | A1 | 9/2008 | Locke et al. |
| 2009/0216205 | A1 | 8/2009 | Ryan et al. |
| 2009/0299306 | A1 | 12/2009 | Buan |
| 2010/0022990 | A1 | 1/2010 | Karpowicz et al. |
| 2010/0155465 | A1 | 6/2010 | Mollstam et al. |
| 2010/0244780 | A1 | 9/2010 | Turner et al. |
| 2011/0006876 | A1 | 1/2011 | Moberg et al. |
| 2011/0060300 | A1 | 3/2011 | Weig et al. |
| 2011/0076170 | A1 | 3/2011 | Fujisaki et al. |
| 2011/0196291 | A1 | 8/2011 | Vischer et al. |
| 2012/0078181 | A1* | 3/2012 | Smith .................. H02J 7/0029 604/404 |
| 2012/0109083 | A1 | 5/2012 | Coulthard et al. |
| 2012/0289913 | A1 | 11/2012 | Eckstein et al. |
| 2013/0012772 | A1 | 1/2013 | Gunday et al. |
| 2013/0025692 | A1 | 1/2013 | Heide et al. |
| 2013/0053795 | A1 | 2/2013 | Coulthard et al. |
| 2013/0131616 | A1 | 5/2013 | Locke |
| 2013/0237937 | A1 | 9/2013 | Ramella et al. |
| 2013/0274718 | A1 | 10/2013 | Yao et al. |
| 2014/0023533 | A1 | 1/2014 | Ishii et al. |
| 2014/0276488 | A1 | 9/2014 | Locke et al. |
| 2015/0174320 | A1 | 6/2015 | Grant et al. |
| 2015/0231021 | A1 | 8/2015 | Smith et al. |
| 2015/0246164 | A1 | 9/2015 | Heaton et al. |
| 2015/0320916 | A1 | 11/2015 | Croteau et al. |
| 2016/0015872 | A1 | 1/2016 | Luckemeyer et al. |
| 2016/0015957 | A1 | 1/2016 | Tieck et al. |
| 2016/0101278 | A1 | 4/2016 | Norris et al. |
| 2016/0149418 | A1* | 5/2016 | Jung .................. H02J 7/007194 320/152 |
| 2016/0213843 | A1 | 7/2016 | Despa et al. |
| 2016/0250398 | A1 | 9/2016 | Barr et al. |
| 2016/0271305 | A1 | 9/2016 | Kurihara et al. |
| 2016/0303358 | A1 | 10/2016 | Croizat et al. |
| 2017/0189588 | A1 | 7/2017 | Croizat et al. |
| 2017/0189666 | A1 | 7/2017 | Sealfon et al. |
| 2017/0216501 | A1 | 8/2017 | Armstrong et al. |
| 2017/0224975 | A1 | 8/2017 | Peer et al. |
| 2017/0296716 | A1 | 10/2017 | Middleton et al. |
| 2017/0319758 | A1 | 11/2017 | Eddy et al. |
| 2017/0354767 | A1 | 12/2017 | Carr et al. |
| 2018/0001000 | A1 | 1/2018 | Herwig et al. |
| 2018/0021178 | A1* | 1/2018 | Locke .................. A61F 13/022 602/43 |
| 2018/0104391 | A1 | 4/2018 | Luxon et al. |
| 2018/0140466 | A1 | 5/2018 | Hunt |
| 2018/0250459 | A1 | 9/2018 | Kimball et al. |
| 2018/0318476 | A1 | 11/2018 | Askem et al. |
| 2019/0192744 | A1 | 6/2019 | Greener et al. |
| 2019/0358372 | A1 | 11/2019 | Askem et al. |
| 2020/0121833 | A9 | 4/2020 | Askem et al. |
| 2021/0077670 | A1 | 3/2021 | Long et al. |

FOREIGN PATENT DOCUMENTS

| | | |
|---|---|---|
| EP | 3124059 A1 | 2/2017 |
| EP | 3124060 A1 | 2/2017 |
| FR | 2939320 A1 | 6/2010 |
| GB | 1220857 A | 1/1971 |
| JP | S5647279 U | 4/1981 |
| JP | H01101978 A | 4/1989 |
| JP | H0796029 A | 4/1995 |
| JP | 2007218241 A | 8/2007 |
| JP | 6047279 B2 | 12/2016 |
| WO | WO-0061206 A1 | 10/2000 |

(56) References Cited

FOREIGN PATENT DOCUMENTS

| WO | WO-03081762 A1 | 10/2003 |
|---|---|---|
| WO | WO-2008033788 A2 | 3/2008 |
| WO | WO-2009071924 A1 | 6/2009 |
| WO | WO-2011075706 A1 | 6/2011 |
| WO | WO-2011094410 A2 | 8/2011 |
| WO | WO-2012004298 A1 | 1/2012 |
| WO | WO-2012100624 A1 | 8/2012 |
| WO | WO-2013015827 A2 | 1/2013 |
| WO | WO-2013064852 A1 | 5/2013 |
| WO | WO-2013078214 A1 | 5/2013 |
| WO | WO-2014115819 A1 | 7/2014 |
| WO | WO-2014164655 A1 | 10/2014 |
| WO | WO-2015197462 A1 | 12/2015 |
| WO | WO-2016103031 A1 | 6/2016 |
| WO | WO-2016109048 A1 | 7/2016 |
| WO | WO-2017044138 A1 | 3/2017 |
| WO | WO-2017062042 A1 | 4/2017 |
| WO | WO-2017160412 A1 | 9/2017 |
| WO | WO-2017197357 A4 | 1/2018 |
| WO | WO-2018009873 A1 | 1/2018 |
| WO | WO-2018009880 A1 | 1/2018 |
| WO | WO-2018041854 A1 | 3/2018 |
| WO | WO-2018150263 A1 | 8/2018 |
| WO | WO-2018150267 A2 | 8/2018 |
| WO | WO-2018167199 A1 | 9/2018 |
| WO | WO-2018185101 A1 | 10/2018 |
| WO | WO-2018195101 A1 | 10/2018 |
| WO | WO-2019063467 A1 | 4/2019 |
| WO | WO-2019129581 A2 | 7/2019 |
| WO | WO-2019179943 A1 | 9/2019 |
| WO | WO-2019211730 A1 | 11/2019 |
| WO | WO-2019211731 A1 | 11/2019 |
| WO | WO-2019211732 A1 | 11/2019 |
| WO | WO-2019224059 A1 | 11/2019 |
| WO | WO-2020011690 A1 | 1/2020 |

OTHER PUBLICATIONS

Wikipedia, "Battery Charger," retrieved from https://web.archive.org/web/20181109005000/https://en.wikipedia.org/wiki/Battery_charger, on Nov. 9, 2018, 12 pages.

International Preliminary Report on Patentability and Written Opinion for Application No. PCT/IB2019/053507, dated Nov. 12, 2020, 8 pages.

Jenkins R.W., et al., "Mechanisms of Resistance to Immune Checkpoint Inhibitors," British Journal of Cancer, Jan. 2, 2018, vol. 118, https://doi.org/10.1038/bjc.2017.434 , pp. 9-16.

\* cited by examiner

POWER SOURCE CHARGING FOR NEGATIVE PRESSURE WOUND THERAPY APPARATUS

CROSS-REFERENCE TO RELATED APPLICATIONS

This application is a U.S. national stage application of International Patent Application No. PCT/IB2019/053507, filed Apr. 29, 2019, which claims the benefit of GB Application No. 1806988.0, filed Apr. 30, 2018, each of which is hereby incorporated by reference in its entirety.

FIELD

Embodiments or arrangements disclosed herein relate to methods and apparatuses for dressing and treating a wound with topical negative pressure (TNP) therapy. For example, but without limitation, any embodiment disclosed herein may relate to treating a wound with reduced pressure. As another non-limiting example, any embodiment disclosed herein may relate to apparatuses and methods for controlling the operation of a TNP system.

DESCRIPTION OF RELATED ART

Many different types of wound dressings are known for aiding in the healing process of a human or animal. These different types of wound dressings include many different types of materials and layers, for example, pads such as gauze pads or foam pads. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue edema; encouraging blood flow; stimulating the formation of granulation tissue; removing excess exudates, and may reduce bacterial load and thus reduce the potential for infection of the wound. Furthermore, TNP therapy permits less outside disturbance of the wound and promotes more rapid healing.

SUMMARY

Disclosed embodiments relate to negative pressure wound closure devices, methods, and systems that facilitate closure of a wound. It will be understood by one of skill in the art that the wounds described herein this specification may encompass any wound, and are not limited to a particular location or type of wound. The devices, methods, and systems may operate to reduce the need for repetitive replacement of wound dressing material currently employed and can advance the rate of healing. The devices, methods, and systems may be simultaneously used with negative pressure to remove wound fluids.

In some implementations, a negative pressure wound therapy device includes a negative pressure source configured to provide negative pressure to a wound via a fluid flow path, a power source configured to power the negative pressure source, and a charging circuit configured to monitor a temperature of the power source and charge the power source. The charging circuit can be further configured to in response to a determination that the temperature of the power source is below a temperature threshold, provide a first charging power to the power source. The charging circuit can be further configured to in response to a determination that the temperature of the power source has reached or is above the temperature threshold, lower the first charging power to a second charging power.

The device of the preceding paragraph can include one or more of the following features. The first charging power can include electrical current at a first amplitude or level and the second charging power can include electrical current at a second amplitude or level, wherein the second amplitude or level is smaller than the first amplitude or level. The charging circuit can be further configured to, while the second charging power is provided to the power source: in response to a determination that the temperature of the power source falls below the temperature threshold, increase the second charging power to the first charging power. The charging circuit can be further configured to stop provision of a charging power to the power source in response to a determination that the power source is substantially charged. The charging circuit can be further configured to, in response to a determination that the temperature of the power source is below a minimum temperature threshold or above a maximum temperature threshold, disable discharging of the power source. The charging circuit can be further configured to disable discharging of the power source by isolating the power source from the negative pressure source.

The device of one or more of preceding paragraphs can include one or more of the following features. The device can include a temperature sensor configured to measure the temperature of the power source, the temperature sensor coupled to the charging circuit. Power source can include at least one battery. The charging circuit can be configured to receive charging power from a power supply and adjust the received charging power to the first or second charging power. The device can further include a power source capacity monitoring circuit configured to monitor remaining capacity of the power source and further configured to indicate at least one of low or critically low remaining capacity of the power source. The device can further include a visual indicator coupled to the power source capacity monitoring circuit, the visual indicator configured to indicate the at least one of low or critically low remaining capacity of the power source.

In some implementations, a method of operating a negative pressure wound therapy device includes by a charging circuit of the negative pressure wound therapy device, monitoring a temperature of a power source of the negative pressure wound therapy device and charging the power source, in response to determining that the temperature of the power source is below a temperature threshold, providing, by the charging circuit, a first charging power to the power source, and in response to determining that the temperature of the power source has reached or is above the temperature threshold, lowering, by the charging circuit, the first charging power to a second charging power.

The method of the preceding paragraph can include one or more of the following features. The first charging power can include electrical current at a first amplitude or level and the second charging power can include electrical current at a second amplitude or level, wherein the second amplitude or level is smaller than the first amplitude or level. The method can further include, by the charging circuit, while providing the second charging power to the power source: in response to determining that the temperature of the power source falls below the temperature threshold, increasing, by the charging circuit, the second charging power to the first charging power. The method can further include, by the charging circuit, stopping provision of a charging power to the power source in response to determining that the power source is substantially charged. The method can further include, by the charging circuit, in response to determining that the temperature of the power source is below a minimum temperature threshold or above a maximum temperature threshold, disabling discharging of the power source. The method can further include, by the charging circuit, disabling discharging of the power source by isolating the power source from the negative pressure source.

The method of one or more of preceding paragraphs can include one or more of the following features. The method can further include measuring with a temperature sensor the temperature of the power source. The power source can include at least one battery. The method can further include, by a power source capacity monitoring circuit, monitoring remaining capacity of the power source and indicating at least one of low or critically low remaining capacity of the power source. The method can further include providing a visual indication of at least one of low or critically low remaining capacity of the power source.

BRIEF DESCRIPTION OF THE DRAWINGS

Other features and advantages of the present disclosure will be apparent from the following detailed description, taken in conjunction with the accompanying drawings of which.

DETAILED DESCRIPTION

Overview

Embodiments disclosed in this section or elsewhere in this specification relate to apparatuses and methods of treating a wound with reduced pressure, including pump and wound dressing components and apparatuses. The apparatuses and components comprising the wound overlay and packing materials, if any, are sometimes collectively referred to in this section or elsewhere in this specification as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, electrical burns, diabetic ulcers, pressure ulcers, stoma, surgical wounds, trauma and venous ulcers or the like.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue edema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Negative Pressure System

Figure 1:
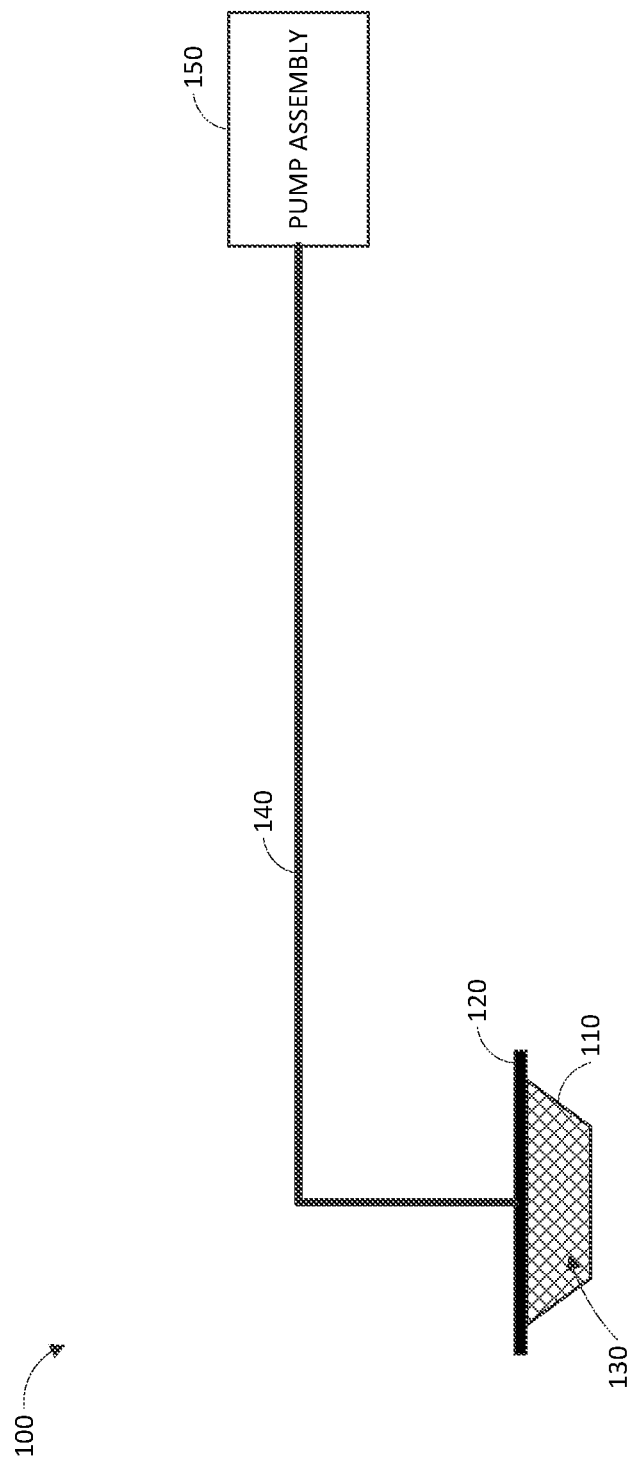
FIG. 1 illustrates a reduced pressure wound therapy system including a pump assembly according to some embodiments.

FIG. 1 illustrates a negative or reduced pressure wound treatment (or TNP) system 100 according to some embodiments. The system 100 comprises a wound filler 130 placed inside a wound cavity 110, the wound cavity 110 sealed by a wound cover 120. In some embodiments, one or more of the wound filler 130, the wound cover 120, or any other component, such as a contact layer (not shown), make up a wound dressing. The system 100 includes a negative pressure wound therapy apparatus or a pump assembly 150 configured to provide reduced pressure to the wound. For example, a conduit 140 having at least one lumen can provide a fluid flow path between the pump assembly 150 and the wound.

Figure 2A:
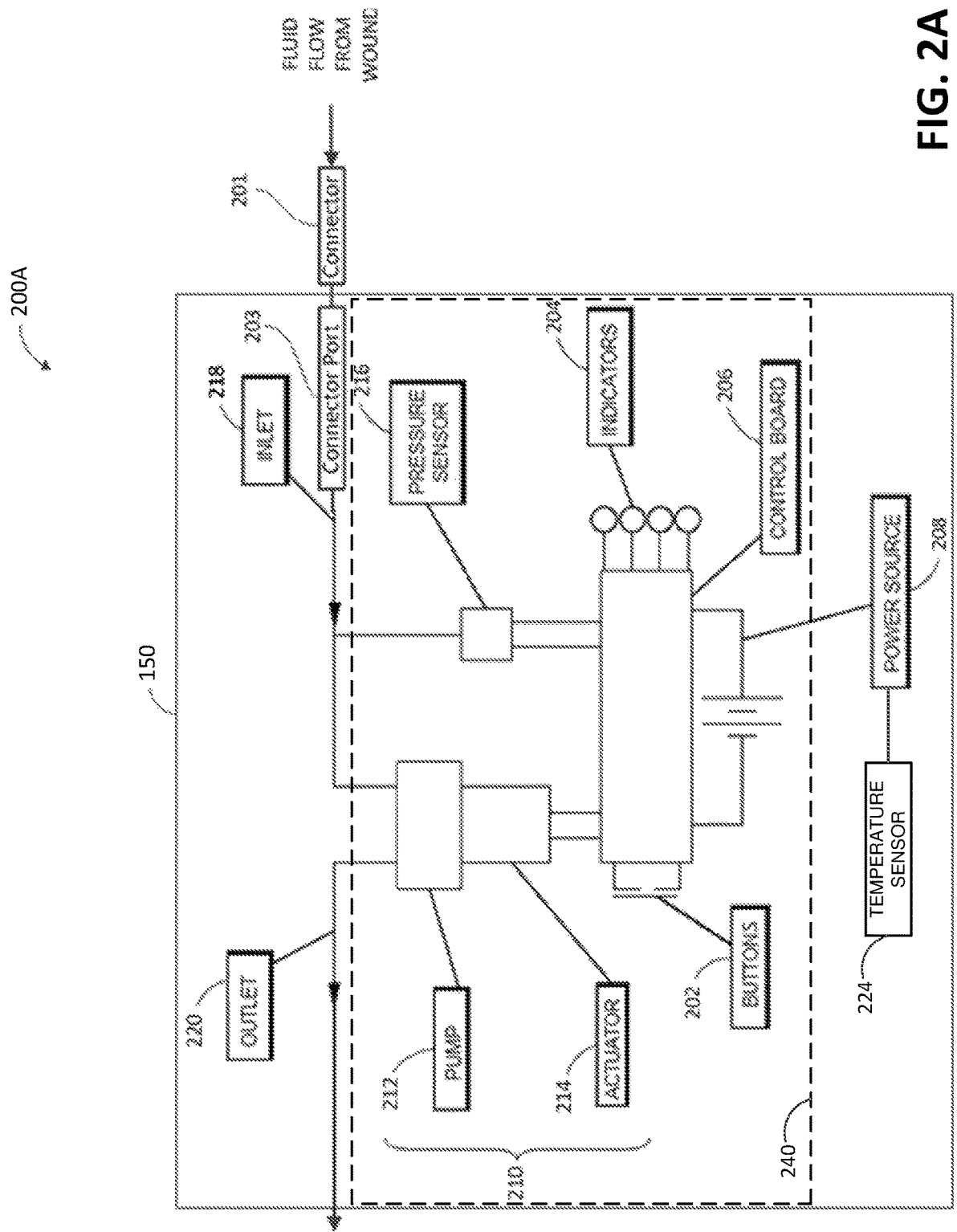
FIG. 2A illustrates a reduced pressure wound therapy system operating in a canisterless mode of operation according to some embodiments.
Figure 2B:
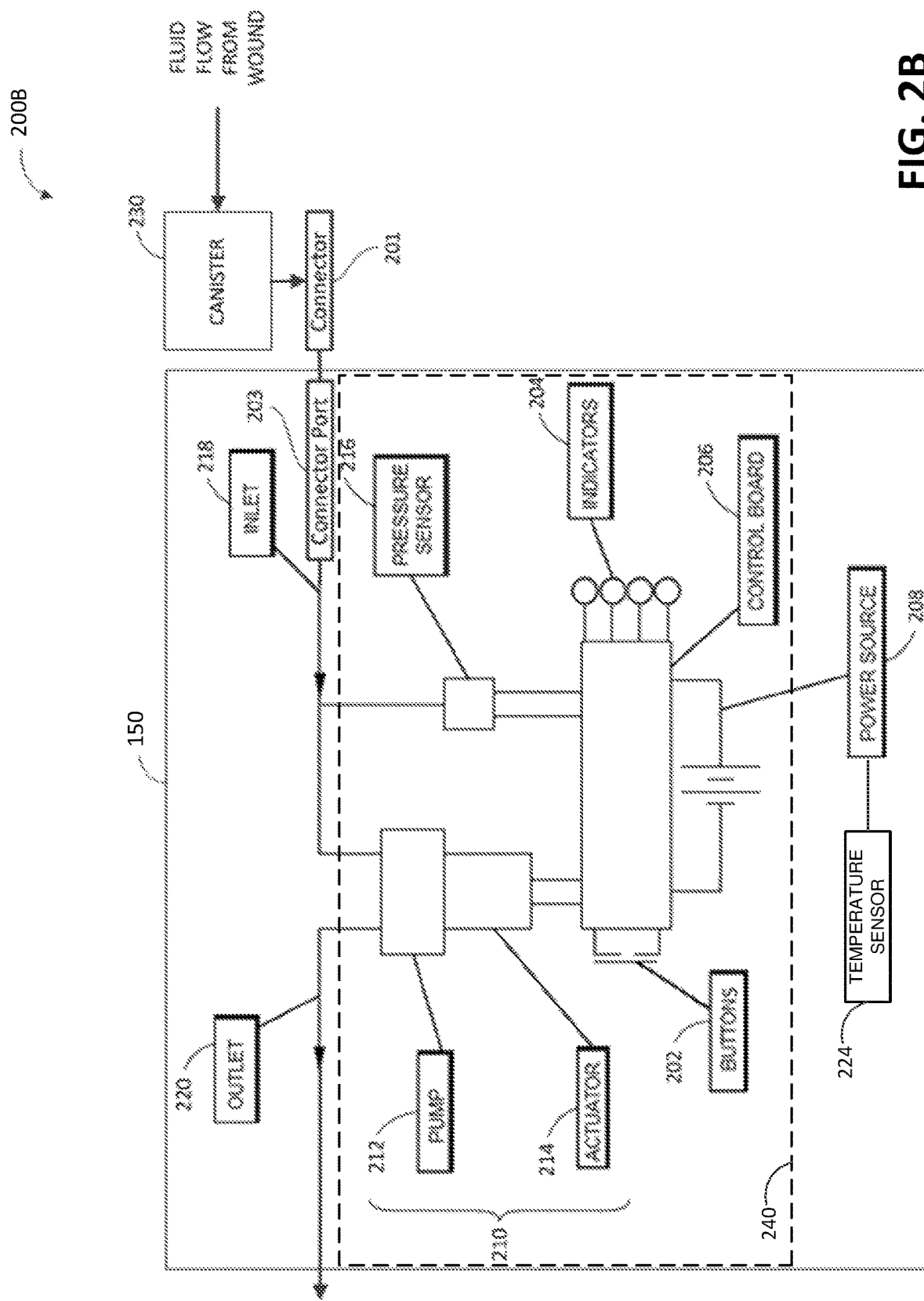
FIG. 2B illustrates a reduced pressure wound therapy system operating in a canister mode of operation according to some embodiments.

FIGS. 2A-2B illustrate that the reduced pressure wound therapy system can be configured to operate with and without a canister (for example, in canister and canisterless modes) according to some embodiments. FIG. 2A shows an embodiment of the TNP system 200A that has a wound dressing connected directly to the pump assembly 150 (for example, canisterless mode). FIG. 2B shows an embodiment of the TNP system 200B that has a canister 230 interposed between the wound dressing and the pump assembly 150 (for example, canister mode). At the beginning of the application of negative pressure wound therapy to a wound when the wound is in the early stages of the healing process and exudes a significant volume of exudate, the reduced pressure wound therapy system may operate with a canister. In this mode of operation, the negative pressure wound therapy system may operate with a foam or gauze RENASYS™ dressing sold by Smith & Nephew or any other suitable dressing. Operation of the reduced pressure wound therapy system with a canister may sometimes be referred to herein as "RENASYS", "RENASYS-mode", or derivatives thereof. As the wound is progressing through the healing process and is starting to exude a smaller volume of exudate, the canister may be removed and the negative pressure wound therapy system may operate with an absorbent dressing, such as the PICO™ dressing sold by Smith & Nephew or any other suitable dressing that retains the wound exudate within the dressing. Operation of the reduced pressure wound therapy system without a canister may sometimes be referred to herein as "PICO", "PICO-mode", or derivatives thereof.

The pump assembly 150 can include one or more switches or buttons 202, one or more indicators 204, and a control board 206. The one or more buttons 202 and the one or more indicators 204 (which collectively make up a user interface) can be in electrical communication with the control board 206, which can include one or more controllers and memory. The one or more buttons 202 can be used for any suitable purpose for controlling an operation of the pump assembly 150. For example, the one or more buttons 202 can be used to activate the pump system 150, pause the pump assembly 150, and clear system indicators such as one or more of the one or more indications 204. The one or more buttons 202 can by any type of switch or button, such as a touchpad, touch screen, keyboard, and so on. In some embodiments, the one or more buttons 202 can be a press button. In various implementations, one or more buttons 202 can be included on a touchscreen interface.

The pump assembly 150 can include a connector port 203 adapted to receive a connector 201. The connector 201 can be a part of the canister or the wound dressing that is attached to the pump assembly 150, as described herein. The connector 201 can be removably attached to the connector port 203. In some arrangements, a first connector 201 can be removed from the pump assembly 150 and replaced with a second connector 201 that is then attached to the pump assembly 150. For example, a first connector 201 that is connected to a RENASYS™ dressing can be removed from the connector port 203 and replaced with a second connector 201 that connected to a PICO™ dressing, thereby allowing the pump assembly 150 to be switched from canister to a canisterless mode of operation. As described in more detail below, the connector 201 and/or pump assembly 150 can be adapted to allow the pump assembly 150 to detect whether a canister or canisterless connector 201 is attached to the connector port 203. In some arrangements, the operation of the pump assembly 150 can be adjusted according to whether the pump assembly 150 detects a canister or a canisterless connector 201 is connected to the connector port 203.

In some embodiments, the connector port 203 can include one or more connector switches in electrical communication with the control board 206, which can include one or more controllers. The one or more connector switches can be configured to engage one or more connectors of the canister or the dressing. In some embodiments, the one or more connector switches can advantageously permit the pump assembly 150 (e.g., the control board 206) to differentiate between a canister connection and a dressing connection. In some embodiments, one or more of the connectors 201 can include one or more connector switches in addition to or in lieu of the one or more connector switches of the connector port 203. The connector switches contemplated herein can be mechanical, electrical, optical, and/or magnetic, or any other suitable switch, and can include sensors and the like. The connector switches can be configured to close or open an electrical circuit, thereby permitting the control board 206 to detect whether the connector switch is engaged or disengaged. For example, as described in more detail below, the connector port 203 can include a connector switch that is actuated by a portion of a connector 201 that couples a canister to the connector port 203. The connector switch can be further configured so that the switch is not actuated by a connector 201 that couples a dressing to the connector port 203, thereby allowing the control board 206 to detect whether a canister or a dressing is attached to the connector port 203. In some arrangements, the pump assembly 150 can be configured so that the connector switch is activated by a connector 201 that couples a dressing to the connector port 203 and is not activated by a connector 201 that couples a canister to the connector port 203.

With continued reference to FIG. 2A, the one or more indicators 204 can indicate one or more operating or failure conditions of the pump assembly 150. Each of the one or more indicators 204 may provide an indication regarding a different operating or failure condition. In some implementations, an active (such as, lit) visual indicator (such as, LED) of the one or more indicators 204 can represent a certain operation condition for the pump assembly 150. For example, a dressing indicator of the one or more indicators 204 can provide an indication as to presence of leaks in the TNP system 100, and an active dressing indicator can represent a leak. As another example, a dressing capacity indicator of the one or more indicators 204 can provide an indication as to the remaining fluid capacity of the wound dressing or canister, and an active dressing capacity indicator can represent that the wound dressing or canister is at or nearing capacity. As yet another example, a power source indicator of the one or more indicators 204 can provide an indication as to remaining capacity or life of the power source 208, such as one or more batteries, and an active power source indicator can represent a low capacity. In some embodiments, the one or more indicators 204 can represent a combination of one or more of the above operating or failure conditions of the pump assembly 150 or other operating or failure conditions for the pump assembly 150.

In some implementations, the one or more indicators 204 can be icons. For example, the one or more indicators 204 can be activated (e.g., lit) via an illumination source such as LEDs (not shown) of pump assembly 150. The one or more indicators 204 can, for instance, be of a different color, two different colors (e.g., two indicators can share the same color), or same color. In some embodiments, the pump assembly 150 can include visual, audible, tactile, and other types of indicators or alarms configured to signal to the user various operating conditions. Such conditions include system on/off, standby, pause, normal operation, dressing problem, leak, error, and the like. The indicators can include speakers, displays, light sources, etc., or combinations thereof. In various implementations, one or more buttons indicators 204 can be included on a touchscreen interface.

The pump assembly 150 can be powered by a power source 208 such as a one or more battery cells or any other suitable power source. Battery cells can include any combination of one or more of lithium-ion, lithium-polymer, lithium iron phosphate, lead acid, nickel based, alkaline, or the like. A temperature sensor 224 can monitor the temperature of the power source 208. In some embodiments, multiple power sources and temperature sensors can be used. The temperature sensor 224 can be a thermistor, thermocouple, or the like. In certain implementations, multiple temperature sensors 224 can be used, such as a primary temperature sensor and a secondary temperature sensor present in case the primary temperature sensor fails. The pump assembly 150 can also include a source of negative pressure 210, which can include a pump 212 powered by an actuator 214, such as an electric motor. In some embodiments, the actuator 214 is integrated into the pump 212. The negative pressure source 210 can be a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, a pump operated by a voice coil actuator, or any other suitable pump or micropump or any combinations of the foregoing, The pump assembly 150 can also include one or more pressure sensors 216 that measure pressure in the fluid flow path. The power source 208 can supply power to electro-mechanical components 240 of the pump assembly 150, including one or more of the negative pressure source 210, pressure sensor 216, control board 206, buttons 202, and indicators 204.

The pump assembly 150 can further include an inlet 218 to connect the pump assembly 150 to the wound dressing. For example, the inlet 218 can be connected to the connector port 203 and the connector 201 that is in fluid communication with the wound dressing via a fluid flow path.

The pump assembly 150 can also include an outlet 220. The outlet 220 can vent or exhaust gas to the atmosphere. In some embodiments, a filter (not shown) can be interposed between the outlet 220 and the atmosphere. The filter can provide filtration of the gas prior to venting the gas to the atmosphere. The filter can be a bacterial filter, odor filter, or any combination thereof. In some embodiments, a dampening component (not shown), such as a noise dampening component, can be interposed between the outlet 220 and the atmosphere. The dampening component can reduce the noise generated by the pump assembly 150 during operation. In some implementations, the pump assembly 150 can communicate information, such as information related to provision of negative pressure therapy, to one or more remote devices. Such communication can be performed using a wired or wireless interface.

FIG. 2B illustrates the pump assembly 150 of FIG. 2A with a canister 230 additionally positioned in a fluid flow path between the inlet 218 and the wound dressing. In the illustrated embodiment, the connector 201 fluidically connects the canister 230 to the connector port 203. As discussed further below, the connector 201 can be configured to signal to the pump assembly 150 whether the connector port 203 is connected to a wound dressing directly or whether a canister 230 is disposed between the connector 203 and the wound dressing.

In some embodiments, the control board 206 (for example, a controller) adjusts one or more operational parameters of negative pressure wound therapy depending on whether the pump assembly is connected to the canister or the dressing. For example, in canisterless mode, the level of negative pressure provided to the wound can be reduced compared to canister mode because the wound is exuding a smaller amount of fluid. As another example, detection of one or more operating conditions can be enabled, disabled, or adjusted. For instance, in canisterless mode, canister full detection (or blockage detection) and alarming can be disabled and, instead, dressing full detection and alarming can be enabled.

In some embodiments, the pump assembly 150 includes a user interface, such as one or more displays, indicators, lights, buttons, switches, speakers, vibrating elements, etc. The user interface can be adjusted based on detection of a canister. For example, in canister mode, the user interface can include an indicator alerting a user when canister becomes full. In canisterless mode, this indicator can be replaced with an indicator alerting the user when the dressing become full. In some embodiments, the indicators are icons.

Figure 3:
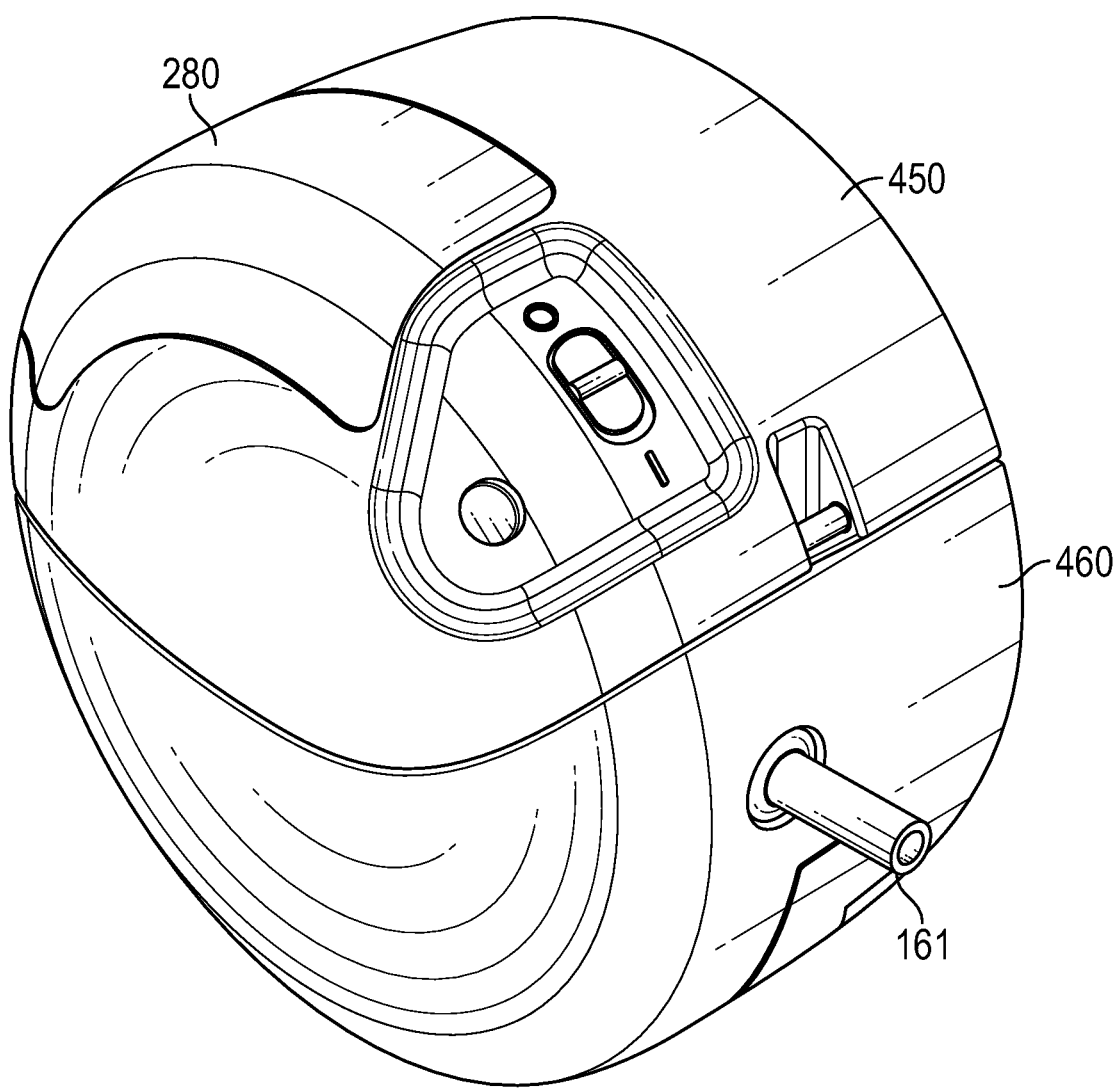
FIG. 3 illustrates a reduce pressure wound therapy apparatus according to some embodiments.

FIG. 3 depicts a perspective view an embodiment of the TNP system according to some embodiments. In the illustrated system, a canister 460 is attached to the pump assembly 450. The canister 460 can have an inlet 161 through which wound exudate can enter the canister 460. In some embodiments, the pump assembly 450 may slide back to disengage the pump assembly 450 from the canister 460. The TNP system can include one or more interchangeable interfaces, for example a panel 280, adapted to be removably attached to a housing. The panel 280 may be configured to indicate a mode of operation of the system, such as the canister mode and canisterless mode.

Power Source Charging

In some embodiments, a power source, such as the power source 208, can be rechargeable. For example, the power source can include one or more batteries that can be charged from a power supply, such as the electrical outlet or mains. Having a rechargeable power source can improve portability of a TNP system and assist with patient mobility. It can be advantageous to charge or recharge the power source quickly, which can be achieved by providing the maximum amount of charging power, such as charging current, to the power source. However, in some cases, charging or recharging the power source should be performed in a safe manner without damaging the power source or any other TNP system components. For example, providing maximum charging power to the power source over a prolonged period of time can cause the power source temperature to rise beyond acceptable level, which can temporarily or permanently damage the power source or other components of the TNP system. As another example, it may not be desirable or safe to charge or recharge or even discharge the power source when the power source temperature is outside of normal operational temperature range, which can be caused by environmental temperature being outside a desired operating range or due to other sources of heat within the TNP system (such as, a motor of the negative pressure source).

In some implementations, a TNP system, which can be any TNP system described herein, can include a charging circuit that monitors and adjusts the charging power so that the power source is charged efficiently and safely. The charging circuit can monitor the temperature of the power source and adjust charging power provided to the power source based on the monitored temperature. For example, the charging circuit can select maximum charging power while the temperature of the power source remains in a safe operational temperature range. This first charging mode can be referred to as fast charging. If the temperature of the power source exceeds a first temperature threshold, which can correspond to the higher temperature of the safe operational temperature range, the charging circuit can lower the charging power provided to the power source. This second charging mode can be referred to as slow charging. The charging circuit can continue monitoring the temperature of the power source when the power source is being charged in the second charging mode. If the temperature of the power source exceeds a second temperature threshold, which can correspond to an acceptable safe operational temperature of the power source, the charging circuit can stop charging the power source, which can prevent damaging the power source or other components of the TNP system. In some embodiments, more than two charging modes with different charging powers can be used, such as three or more charging modes. Accordingly, using multiple charging modes can result in the power source being charged quickly and safely.

In certain implementations, the charging circuit can additionally stop discharging the power source when the temperature of the power source falls below a minimum safe operational temperature threshold or rises above a maximum safe operational temperature threshold. This can be performed in order to prevent causing temporary or permanent damage to the power source or other components of the TNP system. The charging circuit can isolate the power source from electro-mechanical components of the TNP system to stop discharging of the power source.

Figure 4:
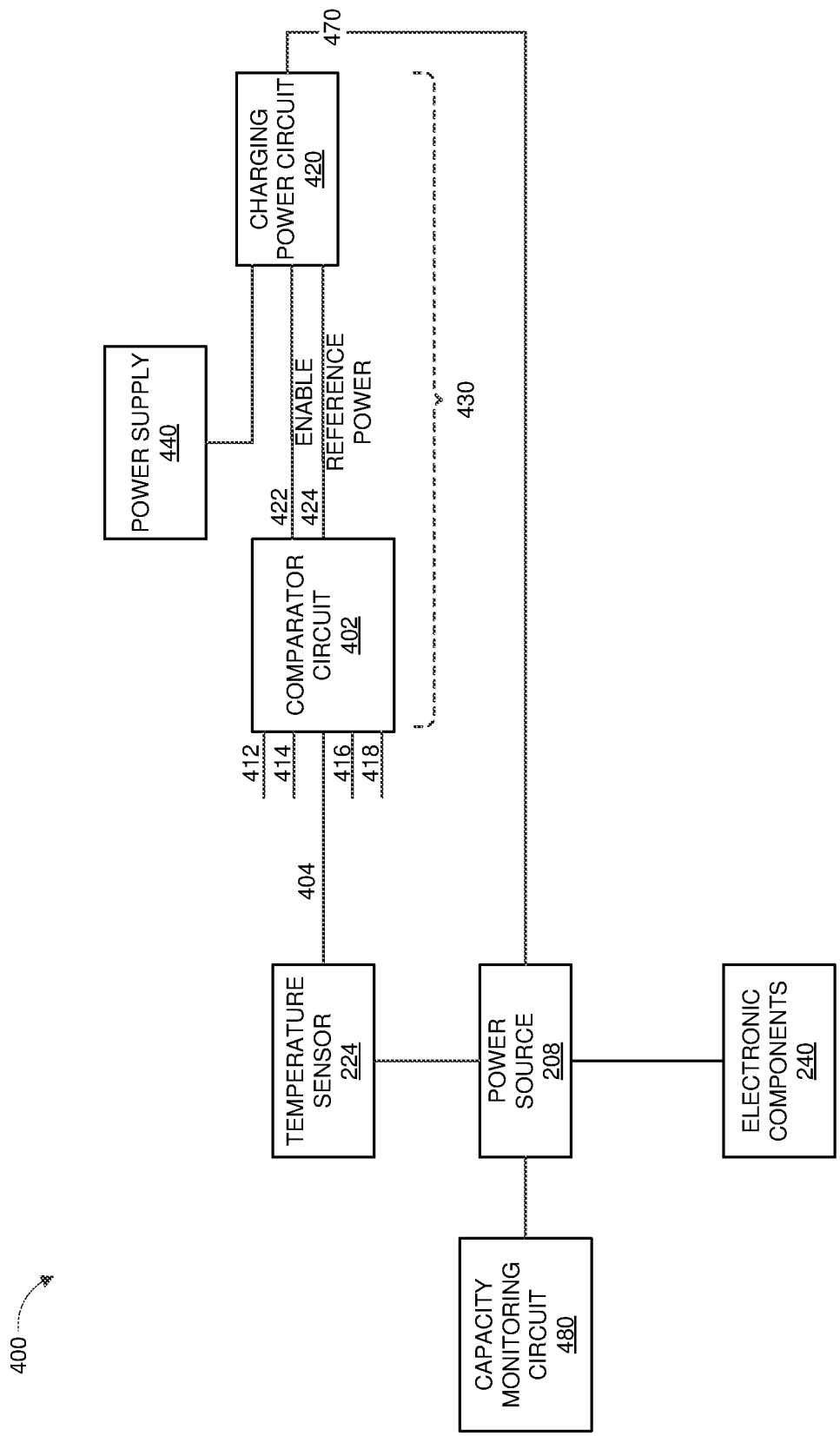
FIG. 4 illustrates a block diagram for power source charging according to some embodiments.

FIG. 4 illustrates a block diagram 400 for power source charging of a TNP system according to some embodiments. The TNP system, such as the system 100 or any other TNP system described herein, can include a power source, such as the power source 208 or any other power source described herein, that supplies power to electro-mechanical components of the TNP system, such as one or more electro-mechanical components 240 as described herein. A temperature sensor, such as the temperature sensor 224, can measure temperature 404 of the power source 208, whose change can be induced by one or more of internal or external causes. A charging circuit 430 can regulate or adjust power provided from a power supply 440, such as the electrical outlet or mains, to suitable charging power 470 for charging the power source 208 depending on the temperature 404. In some implementations, as described herein, the charging circuit 430 can adjust the charging power 470 to charge the power source 280 in the first (fast) and second (slow) charging modes as well as stop the charging and/or discharging of the power source 280 depending on the temperature 404. The charging circuit 430 can use instantaneous temperature measurement or can average a plurality of temperature measurement over a time period to determine the temperature 404.

In certain implementations, a comparator circuit 402 and a charging power circuit 420 can collectively make up the charging circuit 430. Comparator circuit 402 can compare power source temperature 404 to one or more temperature thresholds 412, 414, 416, or 418. Comparator circuit 402 can include one or more analog or digital comparators, such as operational amplifiers. Charging power circuit 420 can adjust power supplied by the power supply 440 based on a reference power 424 determined by the comparator circuit 402 to supply suitable charging power 470 (for example, charging current) to charge the power source 208. Charging power circuit 420 can include one or more current sources or regulators.

In some embodiments, the temperature thresholds 412 and 418 can correspond to the minimum and maximum safe operational temperature thresholds. When the power source temperature 404 falls below the minimum safe operational temperature threshold 412 or rises above the maximum safe operational temperature threshold 412, the charging circuit can stop discharging of the power source 208 by, for example, isolating it from the one or more electro-mechanical components 240. In some cases, temperature threshold 412 can correspond to about 0 degrees Celsius, and temperature threshold 418 can correspond to about 60 degrees Celsius.

In certain implementations, temperature threshold 414 can correspond to the first temperature threshold, which as described herein can correspond to the higher temperature of the safe operational temperature range. In some cases, temperature threshold 414 can correspond to about 40 degrees Celsius. The safe operational temperature range can be bounded by temperature thresholds 412 and 414. As described herein, when the power source temperature 404 remains in the temperature range bounded by temperature thresholds 412 and 414 (or in the safe operational temperature range), the power source 208 can be charged in the first (fast) charging mode. For example, based on determining that the temperature 404 is within the temperature range defined or bounded by temperature thresholds 412 and 414, a first reference power 424 can be provided by the comparator circuit 402 to the charging power circuit 420 to cause the charging power circuit to provide a first (or higher) charging power 470 to the power source 208. In some cases, the first charging power can be current of about 2.5 A or more or less, about 1 A or more or less, or another suitable amplitude or level.

In some embodiments, temperature threshold 416 can correspond to the second temperature threshold, which as described herein can correspond to the acceptable safe operational temperature of the power source above which the charging circuit 430 stops charging the power source. In some cases, temperature threshold 414 can correspond to about 45 degrees Celsius. When the power source temperature 404 exceeds the first temperature threshold 414 but remains below the temperature threshold 416, the power source 208 can be charged in the second (slow) charging mode. For example, second reference power 424 can be provided by the comparator circuit 402 to the charging power circuit 420 to cause the charging power circuit to provide a second (or lower than the first) charging power 470 to the power source 208. In some cases, the second charging power can be current of about 1.75 A or more or less, about 0.5 A or more or less, or another suitable amplitude or level.

In some embodiments, when the power source temperature 404 rises above temperature threshold 416, the charging circuit 430 stops charging the power source. This can be accomplished by the comparator circuit 402 disabling line or signal 422, which can causes the charging power circuit 420 to provide no charging power 470 to the power source 208. When the power source temperature remains in the temperature range between temperature thresholds 412 and 416, the comparator circuit 402 can enable the line or signal 422 to permit the charging power circuit 420 to provide suitable charging power 470 (high or low) to charge the power source 208.

In certain implementations, the temperature range for the first (fast) charging mode can be wider than the temperature range of the second (slow) charging mode. In some embodiments, the charging circuit can decrease the charging power 470 when the power source temperature 404 rises (for example, above temperature threshold 414) to cause transition from the first to the second charging mode and increase the charging power 470 when the power source temperature 404 falls (for example, above temperature threshold 414) to cause transition from the second charging mode to the first charging mode.

In some cases, a capacity monitoring circuit 480 can monitor capacity of the power source 208. This can be performed, for example, to determine if the power source should be charged or if it has been fully charged. Capacity monitoring circuit 480 can, for example, monitor the charge level, voltage, current, or the like of the power source 208. Capacity monitoring circuit 480 can include one or more coulomb counters, resistors, comparators, such as operational amplifiers, or the like. In some cases, the capacity monitoring circuit 480 can include one or more analog to digital converters and can provide digital measurement of the remaining capacity. In some implementations, the capacity monitoring circuit 480 can be part of the charging circuit 430. In some embodiments, the charging circuit 430 and the capacity monitoring circuit 480 can be included in a battery management controller.

In some embodiments, an indication of current charging mode of the power source can be provided to a user. Indication of charging or of current charging mode can be performed in any manner described herein. For example, an indicator 204 (such as, LED) can be lit in different colors or different sequences (such as, solid or flashing sequences) to indicate first and second charging modes. In some implementations, an indication of charging without distinguishing the current charging mode can be provided.

In certain implementations, indication that the power source temperature is below or above minimum or maximum safe operational temperature thresholds can be provided to the user. Such indication can be different than the indication that the power source is charging or is charging in any of the charging modes. Indication that the power source temperature is below or above minimum or maximum safe operational temperature thresholds can be performed in any manner described herein. For example, an indicator 204 (such as, LED) can be lit in a different colors or using a different sequence (such as, solid or flashing sequences).

In some implementations, indication that the power source is fully charged can be provided to the user. Such indication can be different than the indication that the power source is charging or is charging in any of the charging modes or has power source temperature below or above minimum or maximum safe operational temperature thresholds. Indication that the power source if fully charged can be performed in any manner described herein. For example, an indicator 204 (such as, LED) can be lit in a different color or using a different sequence (such as, solid or flashing sequences).

Figure 5:
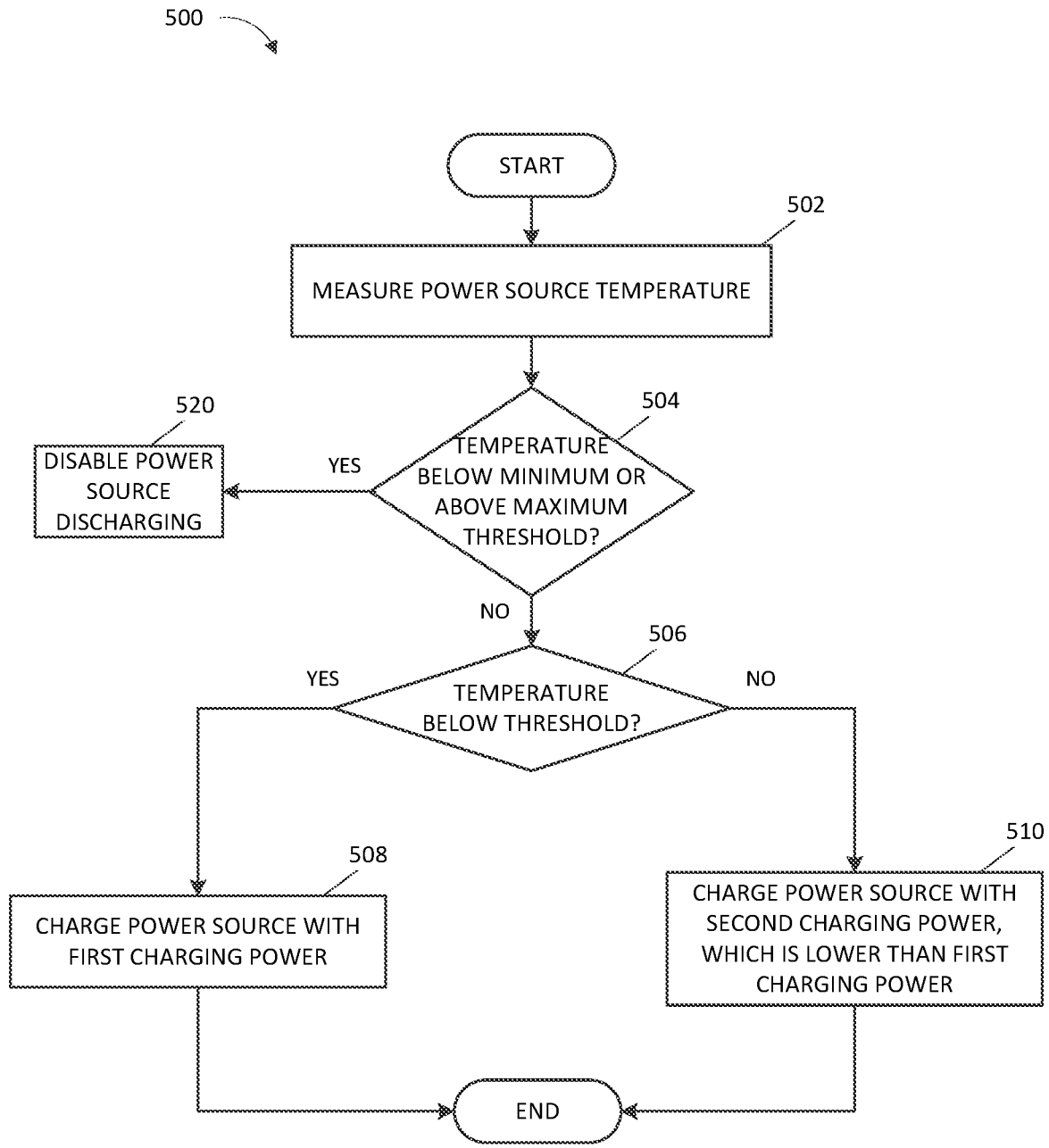
FIG. 5 illustrates a process for power source charging according to some embodiments.

FIG. 5 illustrates a process 500 for power source charging according to some embodiments. In some embodiments, the process 500 can be implemented by the charging circuit 430 alone or in combination with the capacity monitoring circuit 480. In block 502, the process 500 can measure power source temperature as described herein. In block 504, the process can 500 can determine if the power source temperature is below minimum temperature threshold (such as, the minimum safe operational temperature threshold 412) or above maximum temperature threshold (such as, the maximum safe operation temperature threshold 418). If so, the process 500 can transition to block 520 where power source discharge is disabled as described herein.

If the power source temperature is within the temperature range of minimum and maximum temperature thresholds, the process 500 can transition to block 506 where it can determine if the power source temperature is below temperature threshold separating first and second charging modes (such as, the first temperature threshold 414). If the power source temperature is below the temperature threshold, the process 500 can transition to block 508 in which it can charge the power source in a first charging mode by providing first charging power to the power source. If the power source temperature is below the temperature threshold, the process 500 can transition to block 510 in which it can charge the power source in a second charging mode by providing second charging power lower than the first charging power to the power source. The first and second charging modes can correspond to the fast and slow charging modes as described herein.

The process 500 can be performed continuously or periodically by starting in block 502. Although not illustrated in FIG. 5, the process 500 can also disable charging the power source by determining that the power source temperature exceeds the second temperature threshold as described herein. Depending on the measured power source temperature, the process 500 can transition power source charging between disabling discharging of the power source (block 520), disabling charging of the power source (not illustrated), first charging mode (block 508), and second charging mode (block 510).

Monitoring Power Source Capacity

Figure 6:
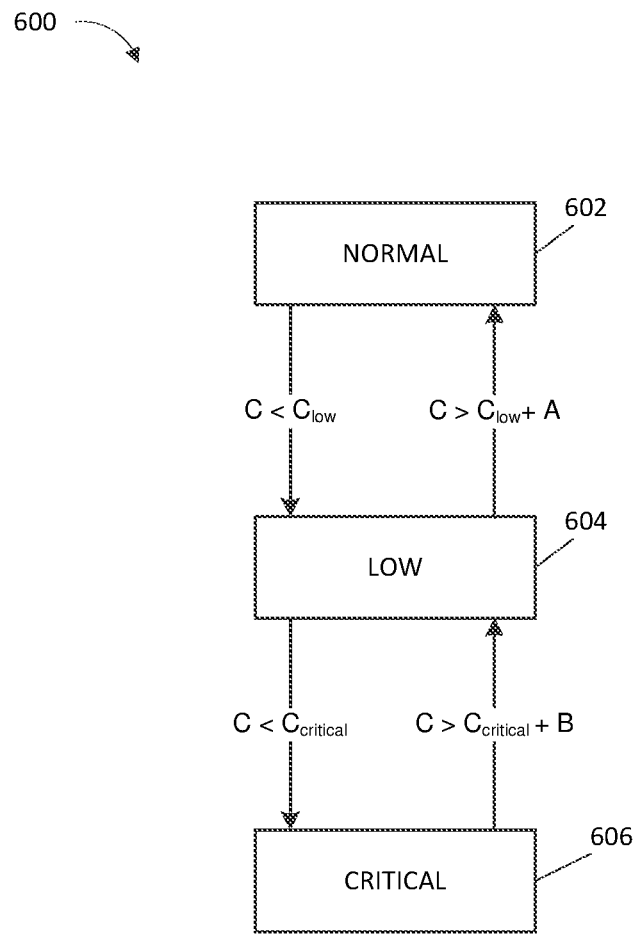
FIG. 6 illustrates a process for monitoring power source capacity according to some embodiments.

FIG. 6 illustrates a process 600 for monitoring power source capacity according to some embodiments. The process 600 can be implemented by the capacity monitoring circuit alone or in combination with the charging circuit 430. The process 600 can continuously or periodically monitor remaining capacity of a power source. The process 600 can compare capacity of the power source (such as, charge, voltage, or current) to one or more capacity thresholds, $C_{low}$ or $C_{critical}$, to determine if the power source capacity corresponds to one of states 602, 604, or 606. State 602 can correspond to normal power source capacity that is above capacity threshold $C_{low}$. State 604 can correspond to low power source capacity that is between capacity thresholds $C_{low}$ and $C_{critical}$. When in state 604, the power source can have sufficient capacity to provide power to one or more electrical components of the TNP system, but the capacity may be getting low and the power source should be charged. State 606 can correspond to critically low power source capacity that is below capacity threshold $C_{critical}$. When in state 606, the power source can have critically low capacity and should be charged immediately or the TNP system may shut down its operation because of insufficient power source capacity.

The process 600 can transition from state 602 to state 604 when the power source capacity falls below capacity threshold $C_{low}$. The process 600 can transition from state 604 to state 602 when the power source capacity rises above capacity threshold $C_{low}$ adjusted by a constant A, which can account for one or more variations or hysteresis in the power source capacity measurements. In some cases, constant A may not be used.

The process 600 can transition from state 604 to state 606 when the power source capacity falls below capacity threshold $C_{critical}$. The process 600 can transition from state 606 to state 604 when the power source capacity rises above capacity threshold $C_{critical}$ adjusted by a constant B, which can account for one or more variations or hysteresis in the power source capacity measurements. In some cases, constants A and B may be the same. In some cases, constant B may not be used.

In some implementations, indication of power source capacity can be provided to the user. Such indication can be different than the indication that the power source is charging or is charging in any of the charging modes, has power source temperature below or above minimum or maximum safe operational temperature thresholds, or is fully charged. Indication of power source capacity can be performed in any manner described herein. For example, an indicator 204 (such as, LED) can be lit in a different color or using a different sequence (such as, solid or flashing sequences) to indicate one or more of normal, low, or critical power source capacities.

Other Variations

Power source charging systems and methods disclosed herein can be used in any TNP system or any medical device. Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensable. Moreover, while illustrative embodiments have been described herein, the scope of any and all embodiments having equivalent elements, modifications, omissions, combinations (for example, of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures may be implemented as software and/or firmware on a processor, controller, ASIC, FPGA, and/or dedicated hardware. Hardware components, such as processors, ASICs, FPGAs, and the like, can include logic circuitry.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A negative pressure wound therapy device comprising:
a negative pressure source configured to provide negative pressure to a wound via a fluid flow path;
a power source configured to power the negative pressure source; and
a charging circuitry configured to monitor a temperature of the power source and charge the power source, the charging circuitry further configured to:
determine that the temperature of the power source is below a first temperature threshold;
in response to determining that the temperature of the power source is below the first temperature threshold, provide a first charging power to the power source;
determine that the temperature of the power source has reached or is above the first temperature threshold;
in response to determining that the temperature of the power source has reached or is above the first temperature threshold, provide a second charging power to the power source, the second charging power being lower the first charging power;
while the second charging power is provided to the power source:
determine that the temperature of the power source has fallen below the first temperature threshold; and
in response to determining that the temperature of the power source has fallen below the first temperature threshold, provide the first charging power to the power source;
determine that the temperature of the power source is below a second temperature threshold;
in response to determining that the temperature of the power source is below the second temperature threshold, disable provision of power by of the power source;
determine that the temperature of the power source is above a third temperature threshold; and
in response to determining that the temperature of the power source is above the third temperature threshold, disable provision of power by the power source.

2. The device of claim 1, wherein the first charging power comprises electrical current at a first amplitude or level and the second charging power comprises electrical current at a second amplitude or level, wherein the second amplitude or level is smaller than the first amplitude or level.

3. The device of claim 1, wherein the charging circuitry is further configured to stop provision of a charging power to the power source in response to a determination that the power source is substantially charged.

4. The device of claim 1, wherein the charging circuitry is further configured to disable provision of power by the power source by isolating the power source from the negative pressure source.

5. The device of claim 1, further comprising a temperature sensor configured to measure the temperature of the power source, the temperature sensor coupled to the charging circuitry.

6. The device of claim 1, wherein the power source comprises at least one battery.

7. The device of claim 1, wherein the charging circuitry is configured to receive a charging power from a power supply and adjust the charging power to the first or second charging power.

8. The device of claim 1, further comprising a power source capacity monitoring circuitry configured to monitor remaining capacity of the power source and further configured to indicate at least one of low or critically low remaining capacity of the power source.

9. The device of claim 8, further comprising a visual indicator coupled to the power source capacity monitoring circuitry, the visual indicator configured to indicate the at least one of low or critically low remaining capacity of the power source.

10. The device of claim 1, wherein the second temperature threshold is below the first temperature threshold, and wherein the third temperature threshold is above the first temperature threshold.

11. A method of operating a negative pressure wound therapy device, the method comprising:
by a charging circuitry of the negative pressure wound therapy device:
monitoring a temperature of a power source of the negative pressure wound therapy device and charging the power source;
at a first time, determining that the temperature of the power source is below a first temperature threshold;
in response to determining that the temperature of the power source is below the first temperature threshold, providing a first charging power to the power source;
at a second time, determining that the temperature of the power source has reached or is above the first temperature threshold;
in response to determining that the temperature of the power source has reached or is above the first temperature threshold, providing a second charging power to the power source, the second charging power being lower than the first charging power;
while providing the second charging power to the power source:
at a third time, determining that the temperature of the power source has fallen below the first temperature threshold; and
in response to determining that the temperature of the power source has fallen below the first temperature threshold, providing the first charging power to the power source;
at a fourth time, determining that the temperature of the power source is below a second temperature threshold;
in response to determining that the temperature of the power source is below the second temperature threshold, disabling provision of power by the power source;

at a fifth time, determining that the temperature of the power source is above a third temperature threshold; and in response to determining that the temperature of the power source is above the third temperature threshold, disabling provision of power by the power source.

12. The method of claim 11, wherein the first charging power comprises electrical current at a first amplitude or level and the second charging power comprises electrical current at a second amplitude or level, wherein the second amplitude or level is smaller than the first amplitude or level.

13. The method of claim 11, further comprising, by the charging circuitry:

at a sixth time, determining that the power source is substantially charged; and in response to determining that the power source is substantially charged, stopping provision of a charging power to the power source.

14. The method of claim 11, wherein disabling provision of power by of the power source comprises isolating the power source from a negative pressure source of the negative pressure wound therapy device.

15. The method of claim 11, further comprising measuring with a temperature sensor the temperature of the power source.

16. The method of claim 11, wherein the power source comprises at least one battery.

17. The method of claim 11, further comprising, by the charging circuitry, receiving a charging power from a power supply and adjusting the charging power to the first or second charging power.

18. The method of claim 11, further comprising, by a power source capacity monitoring circuitry, monitoring remaining capacity of the power source and indicating at least one of low or critically low remaining capacity of the power source.

19. The method of claim 18, further comprising providing a visual indication of at least one of low or critically low remaining capacity of the power source.

20. The method of claim 11, wherein the second temperature threshold is below the first temperature threshold, and wherein the third temperature threshold is above the first temperature threshold.

* * * * *

UNITED STATES PATENT AND TRADEMARK OFFICE
CERTIFICATE OF CORRECTION

PATENT NO. : 11,955,829 B2
APPLICATION NO. : 17/043415
DATED : April 9, 2024
INVENTOR(S) : Matthew Ash Page 1 of 1

It is certified that error appears in the above-identified patent and that said Letters Patent is hereby corrected as shown below:

In the Claims

Column 15, Line 52, Claim 1, after "by" delete "of".

Column 17, Line 21, Claim 14, after "by" delete "of".

Signed and Sealed this
Eighteenth Day of June, 2024

Katherine Kelly Vidal
*Director of the United States Patent and Trademark Office*